United States Patent [19]

Schulte-Elte et al.

[11] Patent Number: 5,155,239

[45] Date of Patent: * Oct. 13, 1992

[54] PREPARATION OF POLYCYCLIC ETHERS

[75] Inventors: Karl-Heinrich Schulte-Elte, Onex, Switzerland; Roger L. Snowden, Viry, France; Claudio Tarchini, Carouge, Switzerland; Béatrice Baer, Grand-Lancy, Switzerland; Christian Vial, Le Lignon, Switzerland

[73] Assignee: Firmenich S.A., Geneva, Switzerland

[*] Notice: The portion of the term of this patent subsequent to Oct. 13, 2008 has been disclaimed.

[21] Appl. No.: 731,831

[22] Filed: Jul. 16, 1991

Related U.S. Application Data

[62] Division of Ser. No. 539,113, Jun. 15, 1990, Pat. No. 5,077,417.

[30] Foreign Application Priority Data

Jun. 19, 1989 [CH] Switzerland ............... 2277/89

[51] Int. Cl.$^5$ ............... C07D 311/74; C07D 307/79
[52] U.S. Cl. ............................. 549/398; 549/462
[58] Field of Search ..................... 549/398, 462

[56] References Cited

U.S. PATENT DOCUMENTS 4,503,290  3/1985  Staiger et al. ............... 549/458
4,613,710  9/1986  Buchi et al. ............... 549/458

FOREIGN PATENT DOCUMENTS 0165458 12/1985 European Pat. Off. .
0170955  2/1986 European Pat. Off. .
2848095  5/1980 Fed. Rep. of Germany .

OTHER PUBLICATIONS

Stevens et al., Tetrahedron, 28, pp. 1939-1944 (1972).
Banthorpe et al., J. C. S. Perkin I, pp. 1637-1644 (1974).
Neumann et al., Chem. Biol. Hoppe-Seyler, 367, pp. 723-729.
Garst et al., Total Synthesis of Manoalide, Tetrahedron Letters, vol. 27, No. 38, pp. 4533-4536 (1986).
Brunke et al., Kationische Cyclisierung von (2)-Und (E)-1,3-Dimethyl-2-(3-Hexenyl)-2-cyclohexenol, Tetrahedron Letters, vol. 22, No. 52, pp. 5259-5262 (1981).
Amoo et al., Synthesis of (S)-Manoalide Diol and the Absolute Configuration of Natural Manoalide, Tetrahedron Letters, vol. 29, No. 20, pp. 2401-2404 (1988).
Chemical Abstracts, vol. 114, No. 15, No. 143747g, "Preparation of Cyclic Terpenes".
Saito et al. Cyclization of E,E-Homofarnesic Acid and Its Related Compounds, Chemistry Letters, pp. 591-594 (1984).
Ohloff et al., Significance of the Geminol Dimethyl Group in the Odor Principles of Ambrox, Helvita Chemical Acta, vol. 68, pp. 2022-2029 (1985).
Ohloff et al., Conformation-Odor Relationship in Nor-labdane Oxides, Helvita Chemica Acta, vol. 69, pp. 163-173 (1986).
Vlad et al. Synthesis of 3a,6,6,9a-Tetramethyl-trans-Perhydronaptho [2,1-b] Furan and 4a,7,7,10a-Tetramethyl-trans-Perhydronaptho [2,1-b] Pyran, Translated from Khimiya Geterotsiklicheskikh Soedinenii, No. 7, pp. 896-901 (Jul. 1990).
Chemical Abstracts, vol. 112, No. 76926h, Method of Producing 3a,6,6,9a-tetramethylperhydronaptho [2,1-b] furan (1990).

*Primary Examiner*—Bernard Dentz
*Attorney, Agent, or Firm*—Pennie & Edmonds

[57] ABSTRACT

Process for the preparation of polycyclic ethers of formula

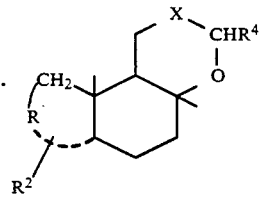

wherein X represents —$(CH_2)_n$—, index n stands for integer 0 or 1, symbol $R^4$ designated a hydrogen atom or a methyl radical, $R^2$ identical or different, represent each a hydrogen atom or a lower alkyl radical from $C_1$ to $C_3$ and R designates either a $C_1$ to $C_6$ linear or branched alkyl radical, or a substituted or unsubstituted alkenyl radical having 2 or 3 carbon atoms in the main chain, said alkenyl radical forming a ring such as indicated by the dotted line, which process comprises the cyclization by means of an acidic agent of an unsaturated compound:

a) of formula

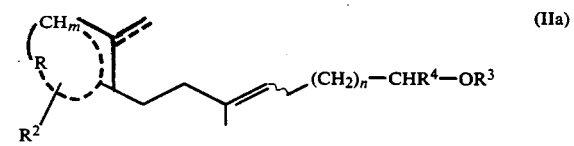

(IIa)

having a double bond in one of the positions indicated by the dotted lines, and wherein index m defines an integer number equal to 1 or 2, symbol $R^3$ stands for a hydrogen atom or a protecting group of the hydroxyl function bound to the oxygen atom and able to dissociate itself from the latter under the reaction conditions, the wavy line represents a C—C bond of cis or trans configuration and index n and symbols R, $R^2$ and $R^4$ are defined as above; or b) of formula

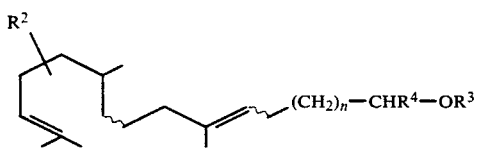 (IIb)
wherein symbols $R^2$, $R^3$ and $R^4$, index n and the wavy line are defined as above; or
c) of formula
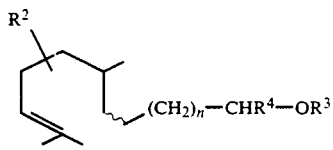 (IIc)
wherein symbols $R^2$, $R^3$ and $R^4$, index n and the wavy line are defined as above.
Some of the compounds (I) are novel and can be used in the perfume industry.
1 Claim, No Drawings

PREPARATION OF POLYCYCLIC ETHERS

This is a division of application Ser. No. 07/539,113, filed Jun. 15, 1990, now U.S. Pat. No. 5,077,417.

BRIEF DESCRIPTION OF THE INVENTION

The present invention relates to a novel process for the preparation of polycyclic ethers of formula

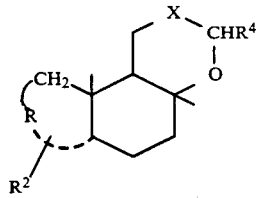

wherein X represents —$(CH_2)_n$—, index n stands for integer 0 or 1, symbol $R^4$ designates a hydrogen atom or a methyl radical, $R^2$ represents a hydrogen atom or a lower alkyl radical from $C_1$ to $C_3$ and R designates either a $C_1$ to $C_6$ linear or branched alkyl radical, or a substituted or unsubstituted alkenyl radical having 2 or 3 carbon atoms in the main chain, said alkenyl radical forming a ring such as indicated by the dotted line, which process comprises the cyclization by means of an acidic agent of an unsaturated compound:
a) of formula

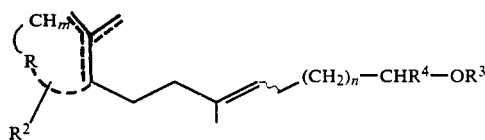

having a double bond in one of the positions indicated by the dotted lines, and wherein index m defines an integer number equal to 1 or 2, symbol $R^3$ stands for a hydrogen atom or a protecting group of the hydroxyl function bound to the oxygen atom and able to dissociate itself from the latter under the reaction conditions, the wavy line represents a C—C bond of cis or trans configuration and index n and symbols R, $R^2$ and $R^4$ are defined as above; or
b) of formula

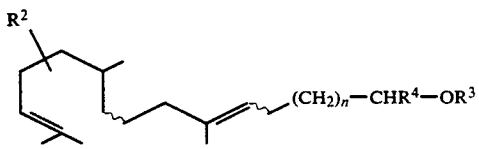

wherein symbols $R^2$, $R^3$ and $R^4$, index n and the wavy line are defined as above; or
c) of formula

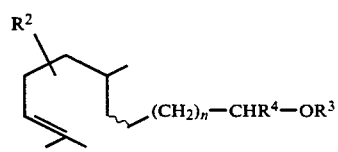

wherein symbols $R^2$, $R^3$ and $R^4$, index n and the wavy line are defined as above.

The invention also relates to novel compounds of formula (I) wherein $R^2$ stands for a methyl radical and to their use as perfuming ingredients in the preparation of perfuming compositions and perfumed articles.

Another object of the present invention is an isomeric mixture of polycyclic ethers of formula

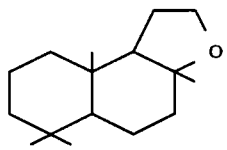

containing a preponderant amount of isomer 3aα,5aβ,-9aα,9aβ-dodecahydro-3a,6,6,9a-tetramethyl-naph-tho[2,1-b]furan.

BACKGROUND OF THE INVENTION

In commercial preparations, the compound of formula

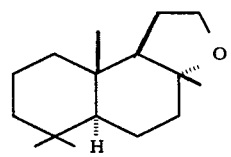

or 3aα,5aβ,9aα,9bβ-dodecahydro-3a,6,6,9a-tetramethyl-naphtho[2,1-b] furan, known under the commercial name of AMBROX ® (origin: Firmenich SA, Geneva), is often accompanied by variable amounts of its diastereoisomers, amongst which epi-AMBROX and iso-AMBROX.

Ever since its discovery [see Helv. Chim. Acta 33, 1251 (1950)], there have been many reported processes for the preparation of this compound. Said processes are generally based on a reaction of oxidative degradation of terpenes such a (—)-sclareol or (+)-manol, or on the use of ambreine as starting material [G. Ohloff in "Fragrance Chemistry", ed. Ernst T. Theimer, p. 545 and following, Academic Press (1982)]. All these materials are of natural origin and therefore their availability and quality are dependent on variable climatic conditions and particular socio-economical factors.

In addition, since they are extracted from natural sources with modest yields, they are available at a price which renders their use on an industrial scale uneconomical.

A process disclosing the cyclization of homofarnesic acid into norambreinolide, followed by the reduction of the obtained lactones and the cyclization of the resulting diol to provide the desired furan derivative, has been reported in European Patent no. 107 857. According to this process, the cyclization of homofarnesic acid is achieved by means of $SnCl_4$.

A similar synthetic approach had been suggested by A. Saito et al. [Chemistry Letters 757 (1981)]. These authors had realized the cyclization of trans-β-monocyclohomofarnesic acid using same $SnCl_4$ as cyclization agent. The two cited documents, incidentally, represent an extension of the work done by G. Lucius on the cyclization of homofarnesic acid [Angew. Chem. 68, 247 (1956); Arc. Pharm. 291, 57 (1958) and Chem. Ber. 93, 2663 (1960)].

Recently, S. Neumann and H. Simon [Biol. Chem. Hoppe-Seiler 367 (8), 723 (1986)] described the formation of 3a,6,6,9a-tetramethyl-perhydronaphtho[2,1-b]furan by an enzymatic cyclization of homofarnesol or of homofarnesyl-(1,5,9-trimethyl-4,8-decadienyl)ether. However, for the moment, such a process has only a purely academic interest, due to the particular nature of the reagents employed, as well as to the observed yields and conversion rates.

The special contribution that AMBROX makes to the perfume industry and the need to have it at a lower market price prompted us to reexamine the available processes for its synthesis. The present invention brings a novel and original solution to this problem.

THE INVENTION

One object of the present invention is to provide a process for the preparation of polycyclic ethers of formula

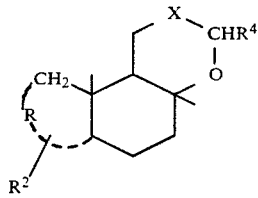

wherein X represents $-(CH_2)_n-$, index n stands for integer 0 or 1, symbol $R^4$ designates a hydrogen atom or a methyl radical, $R^2$ represent a hydrogen atom or a lower alkyl radical from $C_1$ to $C_3$ and R designates either a $C_1$ to $C_6$ linear or branched alkyl radical, or a substituted or unsubstituted alkenyl radical having 2 or 3 carbon atoms in the main chain, said alkenyl radical forming a ring such as indicated by the dotted line, which process comprises the cyclization by means of an acidic agent of an unsaturated compound
a) of formula

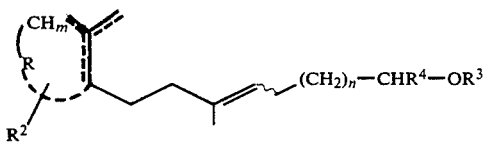
(IIa)

having a double bond in one of the positions indicated by the dotted lines, and wherein index m defines an integer number equal to 1 or 2, symbol $R^3$ stands for a hydrogen atom or a protecting group of the hydroxyl function bound to the oxygen atom and able to dissociate itself from the latter under the reaction conditions, the wavy line represents a C—C bond of cis or trans configuration and index n and symbols R, $R^2$ and $R^4$ are defined as above; or
b) of formula

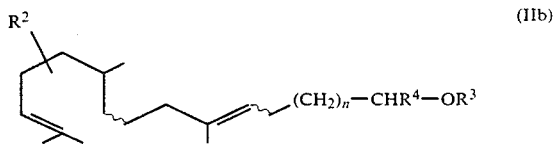
(IIb)

wherein symbols $R^2$, $R^3$ and $R^4$, index n and the wavy line are defined as above; or
c) of formula

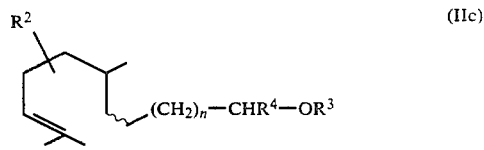
(IIc)

wherein symbols $R^2$, $R^3$ and $R^4$, index n and the wavy line are defined as above.

As indicated above, symbol $R^3$ represents a hydrogen atom or a protecting group of the hydroxyl function bound to the oxygen atom and able to dissociate from it under the reaction conditions. In this case, such a protecting group is a radical having a bond with the oxygen atom which is labile under the acidic medium in which the cyclization takes place. Examples of radicals capable of having this function are well-known in the art. In particular, and as an example, one can cite the radicals of the tetrahydropyranyl, trialkylsilyl, tert-butyl or acyl type.

As acidic cyclization agent, a mineral or organic protonic acid can be used, for example, a carboxylic or sulphonic acid, or yet a Lewis type acid. Amongst the mineral acids, one can cite the phosphoric, sulphuric and perchloric acids, the heteropolyacids, for example aqueous $H_3[P(W_3O_{10})_4]$. Acidic diatomaceous earth, acidic resins, such as DOWEX® 50 [origin: Dow Chemical Co. (USA)] or Amberlyst IR-15, or an acidic aluminum oxide can also be used. Amongst the protonic acids, one can yet cite the hydrohalide acids such as hydrogen chloride, hydrogen bromide or hydrogen iodide.

As an active organic acid, trifluoroacetic or acetic acid can be used, in particular, one can also use a mixture of acetic and sulphuric acids, or methanesulphonic acid. Finally, as cited above, Lewis acids can be employed. Particular examples of the latter are trifluoroboroetherate, tin chloride or titanium tetrachloride.

According to a preferred embodiment of the invention, the cyclization reaction takes place in an inert organic solvent. To this end, it can be carried out in a solvent chosen from hydrocarbons such as petroleum ether, halogenated hydrocarbons such as chloroform, methylene chloride or trichloroethane, aromatic hydrocarbons, for example benzene, toluene, chlorobenzene or methoxybenzene, ethers such as dimethyl ether, esters such as ethyl acetate, or nitrogen containing hydrocarbons, for instance nitromethane, nitroethane or nitroisopropane. Finally, solvents such as carbon disulphide or acetonitrile can also be used.

The results obtained with the different cited acidic reagents and the various solvents mentioned above, although perfectly reproducible, vary as a function of the operator's particular choice when using the process according to the invention. The same can be said as regards the temperature used. The cyclization may, in fact, be carried out at a temperature ranging from −60° to +25°-30°. Obviously, the yields and the isomeric ratio of the compounds obtained varies in accordance with the operator's choice. Preferred embodiments of this process are described in the examples that follow. Any combination resulting from a specific choice of acidic agent, solvent, temperature and, of course, starting product is dependent on the nature of the desired final products.

Separation of the products obtained can be easily achieved by simple distillation.

Owing to its easy operation, the process of the invention presents a major industrial interest. It is in fact an economical process which allows the large scale production of polycyclic ethers which were until now of difficult access via the traditional synthetic methods.

The process of the invention is based on a novel type of cyclization. Indeed, the cyclization of a polyene of the type mentioned above having a free or protected hydroxyl group at the end of a chain has never before been reported, or even suggested, in the art. On the other hand, one of the major aspects of this type of cyclization should be pointed out: it is a perfectly stereospecific reaction. This characteristic of the process of the invention makes it possible to obtain polycyclic ethers (I) in one or the other of the desired isomeric forms, as a function of the structure and configuration of the chosen starting material. This unexpected result is of major importance insofar as the properties of the obtained ether, and namely their organoleptic properties, have a marked dependence on their molecular configuration.

More particularly, the process of the invention provides an isomeric mixture having a preponderant content in isomer 3a$\alpha$,5a$\beta$,9a$\alpha$,9b$\beta$-dodecahydro-3a,6,6,9a-tetramethyl-naphtho[2,1-b] furan. In addition, in the case of the cyclization of 4-methyl-6-(2,6,6-trimethyl-1-cyclohexen-1-yl)-3-hexen-1-ol leading to AMBROX, this reaction leads to preferential formation of trans-decalin compounds. In all the experiments carried out, the proportion of cis-decalin compounds was never above 15% of the total weight of the mixture. Now, such isomeric mixtures, whose composition is novel, possess in fact the more pronounced odor properties and constitute therefore choice perfuming ingredients for the perfumer's creative activity.

The same preponderance of trans decalin compounds was also observed in the cyclization of other compounds (IIa), as it will become apparent from the examples presented further on.

Although the process of the invention finds a particular application for the preparation of AMBROX, its use does in fact allow the preparation of varied polycyclic ethers useful in perfumery and it represents therefore a general method, the use of which can bring an original solution to the synthesis of odoriferous compounds, whether known or with new structures. Amongst those whose structure is known, apart from AMBROX, one can cite the bicyclic ether of formula

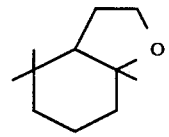

a compound of natural origin appearing in ambergris [Int. Congr. Essent. Oils, 7th, Kyoto, Oct. 7-11, 1977, p. 479; Helv. Chim. Acta 1976, 59, 1140-57], as well as its higher homolog of formula

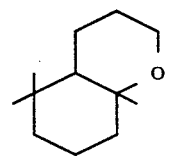

or 1,7,7-trimethyl-2-oxabicyclo[4.4.0]decane described by G. Ohloff et al. [Helv. Chim. Acta 1976, 59, 1140-57].

Concerning the starting products of formula (II), there are some which have already been described in the scientific literature. Such is the case for 4,8,12-trimethyl-3,7,11-tridecenol or (E,E)-homofarnesol, for homogeraniol or for 4-methyl-6-(2,6,6-trimethyl-1-cyclohexen-1-yl)-3-hexen-1-ol, disclosed respectively in Bull. Soc. Chim. France 1960, 1072 and Tetrah. Letters 1988, 29, 2401.

The compounds of formula (IIa) can be obtained, for example, from aldehydes of formula

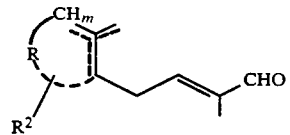

which are either available on the market or can be synthesized from known compounds.

Scheme I illustrates said process for preparing compounds (IIa) from said aldehydes (n=0 in formula IIa):

Scheme I

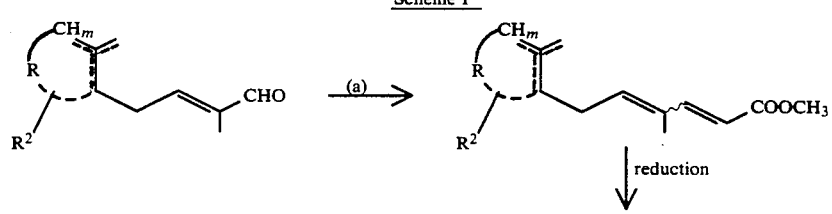

Scheme I

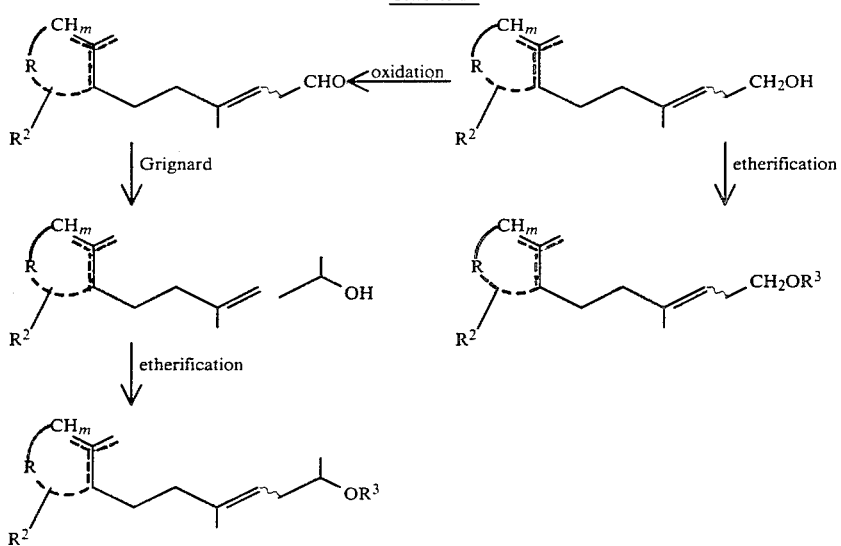

(a) addition reaction of alkyl dialkylphosphonoacetate (ex.: methyl dimethylphosphonoacetate) according to Horner-Emmons [see Chem. Rev. 1974, 74, 87]

Examples of compounds prepared by this method include (E)- and (Z)-4-methyl-6-[2,6,6-trimethyl-1(2)-cyclohexen-1-yl]-3-hexen-1-ol and (E)- and (Z)-4-methyl-6-(2-methylene-6,6-dimethyl-1-cyclohexyl)-3-hexen-1-ol, defined by the following formulae:

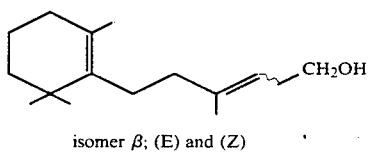

isomer β; (E) and (Z)

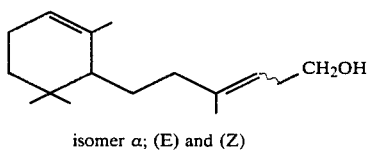

isomer α; (E) and (Z)

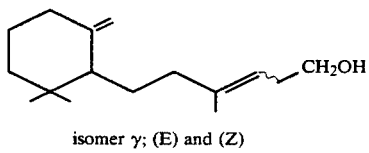

isomer γ; (E) and (Z)

As a reducing agent in step (a) of the above-mentioned process, a metallic reducing agent can be used, such as lithium aluminium hydride, sodium diethyl aluminium hydride (OMH) or yet Vitride.

Other methods for preparing compounds (IIa) can be used and are described in detail in the examples presented hereinafter.

Particular cases of preparation of compounds (IIa) are given in the following examples, wherein the temperatures are indicated in degrees centigrade and the abbreviations have the usual meaning in the art.

EXAMPLE 1

Acid cyclization of (E)- and
(Z)-4-methyl-6-(2,6,6-trimethyl-1-cyclohexen-1-yl)-3-hexen-1-ol, (E)- and
(Z)-4-methyl-6-(2,6,6-trimethyl-2-cyclohexen-1-yl)-3-hexen-1-ol and (E)- and
(Z)-4-methyl-6-(2-methylene-6,6-dimethyl-1-cyclohexyl)-3-hexen-1-ol The cyclization of the first above-mentioned compound was carried out under the reaction conditions described hereinafter. A series of experiments was run while keeping the nature and concentration of the acidic agent constant. To this end, 98% sulphuric acid was used in a 1:1 proportion of acid relative to the starting product.

In most of the experiments carried out, 2.4 g of starting product were used and said product was dissolved in 30 ml of solvent. One single exception was that, when using nitroethane, a smaller amount of solvent was taken.

Generally, the temperature was maintained at −50°, except in the cases where the solvent solidified at this temperature or when the conversion rate was found to be bad.

The results obtained are summarized in the following table:

TABLE

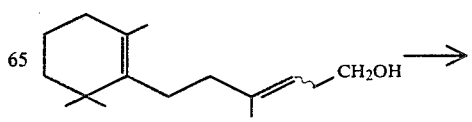

TABLE-continued

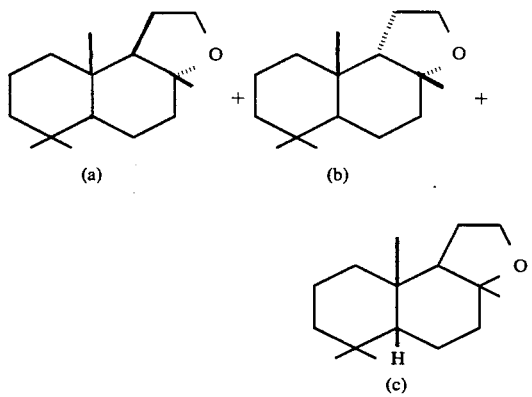

| Experiment no | Solvent | Temp. [°C.] | Products/ Yields (%) | | | Isomer |
|---|---|---|---|---|---|---|
| | | | a | b | c | |
| 1 | CH$_2$Cl$_2$ | −50 | 23 | 5 | 5 | (E) 97% pure |
| 2 | CH$_2$Cl$_2$ | −50 | 4 | 31 | 9 | (Z) 90% pure |
| 3 | CH$_2$Cl$_2$ | −50 | 24 | 19 | 7 | mixture |
| 4 | CH$_2$Cl$_2$ | −50 | 22 | 18 | 7 | (E)/(Z) 2:1 |
| 4 | CH$_2$Cl$_2$ | −50 | 22 | 18 | 7 | ↓ |
| 5 | CH$_2$Cl$_2$ | −20 | 18 | 18 | 8 | ↓ |
| 6 | CH$_2$Cl$_2$ | 0 | 5 | 16 | 9 | ↓ |
| 7 | CHCl$_3$ | −50 | 10 | 15 | 5 | ↓ |
| 8 | CH$_3$CCl$_3$ | −35 | 2 | 2 | 2 | ↓ |
| 9 | toluene | −50 | 5 | 6 | 3 | ↓ |
| 10 | toluene/NMP | −50 | 12 | 12 | 5 | ↓ |
| 11 | chlorobenzene | −40 | 7 | 5 | 3 | ↓ |
| 12 | anisole | −20 | 7 | 4 | 4 | ↓ |
| 13 | acetonitrile | −50 t.a. | 1 | 2 | — | ↓ |
| 14 | CS$_2$ | −40 −20 | 4 | 5 | 4 | ↓ |
| 15 | THF | −50 t.a. | — | — | — | ↓ |
| 16 | petroleum ether | −50 | 2 | 2 | 2 | ↓ |
| 17 | petroleum ether/MeOH | −50 t.a. | — | 4 | 2 | ↓ |
| 18 | MeNO$_2$/CH$_2$Cl$_2$ | −30 | 12 | 16 | 5 | ↓ |
| 19 | nitroethane | −50 −40 | 14 | 20 | 5 | ↓ |
| 20 | nitroethane | −50 −20 | 17 | 23 | 6 | ↓ |
| 21 | nitro-isopropane | −50 −20 | 11 | 13 | 5 | ↓ |

In all of the experiments mentioned above, the reaction was carried out as follows. A solution of the starting alcohol (2.4 g; 8.9 mmol) in 5 ml of solvent was added dropwise over 15 min to a stirred mixture of 98% sulphuric acid (2.4 g; 24 mmol) in 25 ml of solvent at −50° and under N$_2$. After 3 h at −50°, the mixture was neutralized by pouring it into a 10% aqueous solution of NaHCO$_3$. Extraction with ether, followed by the usual separation, neutralization, drying and evaporation treatments, yielded a residue which, once distilled, provided the desired products. Analysis of the distillate was carried out by gas chromatography on a CARBOWAX ® column (10 m, capillary): 130°-170°/4° per min.

Another series of essays was realized by varying the proportion of acid. To this end, the following method was used.

A solution of 2.4 g (8.9 mmol) of an isomer mixture E/Z (2:1) of starting alcohol in 5 ml of CH$_2$Cl$_2$ was added dropwise over 15 min to a mixture of the acid in 25 ml of CH$_2$Cl$_2$ at −50° under N$_2$. The reaction mixture was then treated as described before. The results obtained are summarized in the following table.

TABLE

| Experiment no | Acid | Amount of acid [g] | Products/ Yields (%) | | |
|---|---|---|---|---|---|
| | | | a | b | c |
| 22 | H$_2$SO$_4$ | 1,2 | 6 | 4 | 2 |
| 23 | H$_2$SO$_4$ | 2,4 | 24 | 19 | 7 |
| 24 | H$_2$SO$_4$ | 3,6 | 24 | 18 | 5 |
| 25 | H$_2$SO$_4$ | 4,8 | 27 | 23 | 10 |
| 26 | H$_2$SO$_4$ | 4,8 | 12 | 21 | 9 |
| 27 | H$_2$SO$_4$ | 7,2 | 19 | 20 | 8 |
| 28 | H$_2$SO$_4$ | 9,6 | 5 | 21 | 5 |
| 29 | H$_2$SO$_4$/oleum* | 2,6 | 22 | 17 | 6 |
| 30 | oleum | 2,4 | 18 | 14 | 5 |
| 31 | oleum | 4,8 | 18 | 15 | 5 |

*10:1

Finally, a series of experiments was carried out in order to examine the influence of the proportion of acid used and of the temperature on the cyclization yield and on the nature of the isomers obtained. The ensuing results are summarized in the following table. The operating manner is described hereinafter.

A 30% solution of the starting alcohol, isomeric mixture E/Z 2:1 (2.4 g; 8.9 mmol) in the chosen solvent was added dropwise over 30 min to a stirred mixture of 98% H$_2$SO$_4$. After a reaction time of 30 min to 1 h, during which the reaction mixture was stirred at the temperature indicated in the table, the mixture underwent the usual treatments already described in the preceding experiments. The results obtained are summarized in the following table.

TABLE

| Experiment no | Solvent [ml] | H$_2$SO$_4$ [g] | Temp. [°C.] | Products/ Yields (%) | | |
|---|---|---|---|---|---|---|
| | | | | a | b | c |
| 32 | EtNO$_2$ (10) | 2,4 | −60/−20 | 17 | 23 | 6 |
| 33 | EtNO$_2$ (10) | 4,8 | −60/−40 | 22 | 31 | 7 |
| 34 | EtNO$_2$ (220) | 108 | −60/−40 | 22 | 33 | 8 |
| 35 | EtNO$_2$ (340) | 108 | −60/−40 | 23 | 36 | 7 |
| 36 | EtNO$_2$ (30) | 4,8 | 0 | 5 | 20 | 9 |
| 37 | EtNO$_2$ (30) | 7,2 | −60 | 32 | 29[1] | 4 |
| 38 | EtNO$_2$ (30) | 7,2 | −60 | 1 | 68[2] | 9 |
| 39 | n-PrNO$_2$ (30) | 4,8 | −40 | 21 | 28 | 6 |
| 40 | n-PrNO$_2$ (30) | 7,2 | −60 | 22 | 34 | 6 |
| 41 | i-PrNO$_2$ (30) | 2,4 | −50/20 | 11 | 13 | 5 |
| 42 | i-PrNO$_2$ (30) | 7,2 | −60 | 19 | 36 | 6 |

[1] pure alcohol (E) (97%)
[2] pure alcohol (Z) (90%)

In the majority of the examined reaction conditions, the formation of transdecalin isomers is greatly favored relative to that of their corresponding cis isomers.

The cyclization of 4-methyl-6-(2,6,6-trimethyl-2-cyclohexen-1-yl)-3-hexen-1-ol (alcohol A), in its isomeric forms (E)- and (Z)-, was carried out on 100 mg of starting alcohol in an excess of 98% sulphuric acid (5 mol equiv.) in dichloromethane, at −50° and for 3 h. The reaction mixture was treated in the usual manner described in the above-mentioned experiments.

The same applied to the cyclization of (E)- and (Z)-4-methyl-6-(2-methylene-6,6-dimethyl-1-cyclohexyl)-3-hexen-1-ol (alcohol B).

The following table summarizes the results obtained:

TABLE

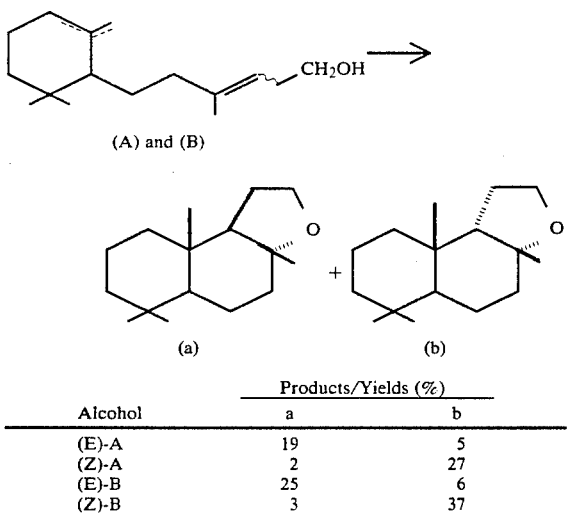

| Alcohol | Products/Yields (%) | |
|---|---|---|
| | a | b |
| (E)-A | 19 | 5 |
| (Z)-A | 2 | 27 |
| (E)-B | 25 | 6 |
| (Z)-B | 3 | 37 |

The alcohols used as starting products in the process described above can be prepared according to the following method.

36 g (0.2 mol) of 30% sodium methylate in methanol were introduced dropwise, under vigorous stirring and $N_2$ atmosphere, into a mixture containing 41.2 g (0.2 mol) of 2-methyl-4-(2,6,6-trimethyl-1-cyclohexen-1-yl)-2-buten-1-al and 40 g (0.22 mol) of methyl dimethylphosphonate. The reaction was exothermic. After the introduction, the mixture was kept at reflux for 1 h. After cooling, 30 ml of water were added and the mixture was extracted with petroleum ether. The organic phase was separated and then washed to neutrality, dried and concentrated.

Distillation on a 10 cm length Vigreux column provided 48.2 g of methyl 4-methyl-6-(2,6,6-trimethyl-1-cyclohexen-1-yl)-2,4-hexadienoate. B.p. 102°/4 Pa; yield 91.5%.

2-Methyl-4-(2,6,6-trimethyl-1-cyclohexen-1-yl)-2-buten-1-al is a commercial product (origin: L. Givaudan).

The ester obtained above was then reduced by means of lithium aluminum hydride according to the following method.

42.8 g (0.163 mol) of methyl 4-methyl-6-(2,6,6-trimethyl-1-cyclohexen-1-yl)-2,4-hexadienoate diluted with an equal volume of THF were added dropwise to a suspension of 6.2 g (0.163 mol) of $LiAlH_4$ in 500 ml of anhydrous THF, under nitrogen. The reaction was exothermic and was kept below 30° by cooling with an icy water bath. The mixture was then heated to reflux during 5 h, then cooled to 10° and, at same temperature, there were added slowly, dropwise, 6.2 ml of water, 6.2 ml of 2N NaOH and finally 18.6 ml of water. The mixture was stirred for yet 5 min and a white precipitate formed, which was then filtered. After concentrating, the clear filtrate was distilled on a 10 cm length Vigreux column under a pressure of 3 Pa. The desired alcohols were thus obtained, in the form of an isomeric mixture (E)/(Z); B.p. 76°/3 Pa; yield 85%.

IR: 3300 cm$^{-1}$.

isomer (E):
IR: 3310, 1462, 1378, 1356, 1200, 1040, 870 cm$^{-1}$.
$^1$H-NMR: 1.00(6H,s); 1.41(2H,m); 1.58(2H,m); 1.61(3H,s); 1.70(3H,s); 1.91(2H,t,J=6.5 Hz); 2.06(4H,s); 2.30(2H,q,J=7 Hz); 3.63(2H,t,J=7 Hz); 5.16(1H,t,J=7 Hz) δ ppm.
MS: M$^+$=236; m/e: 137(77), 121(11), 107(15), 95(100), 81(83), 69(32), 55(35).

isomer (Z):
B.p. 105°–110°/1 Pa.
IR: 3320, 1470, 1442, 1370, 1358, 1200, 1040, 870, 824 cm$^{-1}$.
$^1$H-NMR: 1.02(6H,s); 1.22(2H,m); 1.37(2H,m); 1.64(3H,s); 1.78(3H,s); 1.91(2H,t,J=6 Hz); 2.06(4H,m); 2.31(2H,q,J=7 Hz); 3.63(2H,t,J=6 Hz); 5.11(1H,t,J=7 Hz) δ ppm.
MS: M$^+$=236; m/e: 137(100), 121(9), 107(12), 95(81), 81(51), 69(19).

The isomeric alcohols derived from 2-methyl-4-(2,6,6-trimethyl-2-cyclohexen-1-yl)-2-buten-1-al and from 2-methyl-4-(2-methylene-6,6-dimethyl-1-cyclohexyl)-2-buten-1-al were prepared in an analogous manner. These aldehydes can be prepared according to the methods described by K.-H. Schulte-Elte et al. [Nouv. J. Chim. 1978, 2, 427–30] and I. M. Heilbron et al. [J. Chem. Soc. 1942, 727], respectively.

4-methyl-6-(2,6,6-trimethyl-2-cyclohex-1-yl)-3-hexen-1-ol isomer (E):
B.p. 160°–170°/2 Pa.
IR: 3300, 2900, 1440, 1380, 1360, 1040, 812 cm$^{-1}$.
$^1$H-NMR: 0.87(3H,s); 0.92(3H,s); 1.12(1H,m); 1.30–1.65(4H); 1.65(3H,s); 1.68(3H,s); 1.96(2H,m); 2.05(2H,m); 2.28(2H,q,J=7 Hz); 3.61(2H,t, J=7 Hz); 5.13(1H,t,J=7 Hz); 5.28(1H,s) δ ppm.
MS: M$^+$=236; m/e: 136(74), 121(56), 109(41), 95(26), 81(100), 69(26), 55(31), 41(64).

isomer (Z):
B.p. 160°–170°/2 Pa.
IR: 3320, 2900, 1442, 1380, 1360, 1042, 760 cm$^{-1}$.
$^1$H-NMR: 0.88(3H,s); 0.96(3H,s); 1.14(1H,m); 1.30–1.60(4H); 1.71(3H,s); 1.74(3H,s); 1.96(2H,m); 2.07(2H,m); 2.28(2H,q,J=7 Hz); 3.62(2H,t, J=7 Hz); 5.09(1H,t,J=7 Hz); 5.31(1H,s) δ ppm.
MS: M$^+$=236; m/e: 136(38), 121(31), 109(42), 95(21), 81(100), 69(25), 55(21), 41(62).

4-methyl-6-(2-methylene-6,6-dimethyl-1-cyclohexyl)-3-hexen-1-ol isomer (E):
B.p. 160°–170°/2 Pa.
IR: 3300, 2900, 1640, 1440, 1380, 1360, 1042, 884, 630 cm$^{-1}$.
$^1$H-NMR: 0.84(3H,s); 0.92(3H,s); 1.21(1H,m); 1.35–1.85(7H); 1.64(3H,s); 1.92–2.12(3H); 2.29(2H,q,J=7 Hz); 3.62(2H,t,J=7 Hz); 4.54(1H,s); 4.76(1H,s); 5.12(1H,t,J=7 Hz) δ ppm.
MS: M$^+$=236; m/e: 221(25), 177(25), 121(26), 109(61), 95(38), 81(84), 69(61), 55(41), 41(100).

isomer (Z):
B.p. 160°–170°/2 Pa.
IR: 3300, 2900, 1640, 1440, 1380, 1362, 1042, 884, 630 cm$^{-1}$.
$^1$H-NMR: 0.83(3H,s); 0.92(3H,s); 1.22(1H,m); 1.34–1.70(6H); 1.73(3H,s); 1.80–2.15(4H); 2.25(2H,m); 3.60(2H,t,J=7 Hz); 4.58(1H,s); 4.79(1H,s); 5.11(1H,t,J=7 Hz) δ ppm.
MS: M$^+$=236; m/e: 221(25), 177(27), 121(29), 109(70), 95(42), 81(90), 69(60), 55(47), 41(100).

EXAMPLE 2

Acid cyclization of (E)- and (Z)-4,8-dimethyl-3,7-nonadien-1-ol (homogeraniol and homonerol)

The cyclization of homogeraniol and homonerol was carried out according to the method described in Example 1, by means of sulphuric acid in methylene chloride at −50°. 1,6,6-Trimethyl-2-oxabicyclo[4.3.0]nonane was thus obtained, with the cis/trans isomeric content indicated in the following table:

| Experiment | Starting product | Final product yield (%) | Isomeric ratio cis/trans |
|---|---|---|---|
| 1 | (E)- | 56 | 1:5 |
| 2 | (Z)- | 50 | 6:1 |

The starting products used in the above-described cyclization were prepared by reduction, by means of LiAlH$_4$, of methyl 4,8-dimethyl-3,7-nonadienoate following the method indicated in Example 1.

The analytical characteristics of the two alcohols obtained were as follows:

isomer (E):
IR: 3320, 2910, 1440, 1380, 1040, 880, 830 cm$^{-1}$.
$^1$H-NMR: 1.61(3H,s); 1.65(3H,s); 1.69(3H,s); 2.07(4H); 2.28(2H,dt, J=7.7 Hz); 3.60(2H,t,J=7 Hz); 5.08(1H,t,J=7 Hz); 5.12(1H,t,J=7 Hz) δ ppm.
MS: M$^+$=168; m/e: 125(22), 81(14), 69(100), 53(12), 41(96).

isomer (Z):
IR: 3320, 2900, 1440, 1380, 1040, 878, 830 cm$^{-1}$.
$^1$H-NMR: 1.62(3H,s); 1.69(3H,s); 1.73(3H,s); 2.08(4H); 2.28(2H,dt, J=7,7 Hz); 3.60(2H,t,J=7 Hz); 5.12(1H,m); 5.14(1H,t,J=7 Hz) δ ppm.
MS: M$^+$=168; m/e: 125(22), 81(12), 69(100), 53(13), 41(98).

EXAMPLE 3

Acid cyclization of (E)- and (Z)-4-methyl-6-(2,5,6,6-tetramethyl-2-cyclohexen-1-yl)-3-hexen-1-ol The reaction was carried out following the process described in Example 1 by means of 98% sulphuric acid and at −60°. To this end, 0.7 g of starting (E)-alcohol were treated with 1.4 g of H$_2$SO$_4$ in 5 ml of nitroethane. After stirring for 1 h at −60°, the reaction mixture was poured on ice and the whole extracted with ether. After the usual neutralization and concentration treatments, a bulb-to-bulb distillation of the product was carried out at a temperature of 150°/20 Pa. 0.45 g of methyl-AMBROX were thus obtained, in the form of an isomeric mixture having the following main components:

3aα,5aα,7α,9aα,9bβ-dodecahydro-3a,6,6,7,9a-pentamethyl-naphtho[2,1-b]furan:
$^1$H-NMR: 0.84(3H,d,J=7 Hz); 0.97(3H,s); 0.98(3H,s); 1.05(3H,s); 1.14(3H,s); 3.85(2H,m) δ ppm.
MS: M$^+$=250; m/e: 235(100), 151(29), 137(25), 123(30), 109(30), 97(77), 83(36), 67(33), 55(52), 43(55).

3aβ,5aα,7α,9aα,9bβ-dodecahydro-3a,6,6,7,9a-pentamethyl-naphtho[2,1-b]furan:
$^1$H-NMR: 0.79(3H,d,J=7 Hz); 0.92(3H,s); 0.98(3H,s); 1.09(3H,s); 1.35(3H,s); 3.76(2H,m) δ ppm.
MS: M$^+$=250; m/e: 235(100), 151(27), 137(28), 123(31), 109(31), 97(89), 81(42), 67(37), 55(50), 43(76).

3aβ,5aα7α,9aα,9bα-dodecahydro-3a,6,6,7,9a-pentamethyl-naphtho[2,1-b]furan:
$^1$H-NMR: 0.81(3H,d,J=7 Hz); 0.93(3H,s); 104(3H,s); 1.14(3H,s); 1.15(3H,s); 3.85(2H,m) δ ppm.
MS: M$^+$=250; m/e: 235(88), 151(22), 137(21), 121(25), 109(29), 97(100), 81(26), 67(30), 55(42), 43(42).

3aα,5aα,7α,9aα,9bα-dodecahydro-3a,6,6,7,9a-pentamethyl-naphtho[2,1-b]furan:
$^1$H-NMR: 0.76(3H,d,J=7 Hz); 0.94(3H,s); 0.98(3H,s); 1.02(3H,s); 1.055(3H,s); 3.77(2H,m) δ ppm.
MS: M$^+$=250; m/e: 235(89), 151(17), 135(14), 121(21), 109(26), 97(100), 81(41), 69(34), 55(43), 43(47).

Following the same process, the cyclization of the (Z)-alcohol was carried out, leading to methyl-AMBROX in the form of an isomeric mixture having the following main compounds:

3aα,5aβ,7α,9aα,9bβ-dodecahydro-3a,6,6,7,9a-pentamethyl-naphtho[2,1-b]furan:
$^1$H-NMR: 0.67(3H,s); 0.81(3H,s); 0.845(3H,d,J=7 Hz); 0.90(3H,s); 1.09(3H,s); 3.86(2H,m) δ ppm.
MS: M$^+$=250; m/e: 235(100), 151(33), 137(42), 109(20), 97(47), 81(13), 67(14), 55(16), 43(21).

3aα,5aβ,7α,9aα,9bα-dodecahydro-3a,6,6,7,9a-pentamethyl-naphtho[2,1-b]furan:
$^1$H-NMR: 0.66(3H,s); 0.84(3H,d,J=7 Hz); 0.91(3H,s); 1.07(3H,s); 1.37(3H,s); 3.81(2H,m) δ ppm.
MS: M$^+$=250; m/e: 235(47), 151(100), 137(53), 123(17), 109(22), 95(27), 81(17), 67(17), 55(17), 43(25).

These various isomers were separated by gas chromatography. 4-Methyl-6-(2,5,6,6-tetramethyl-2-cyclohexen-1-yl)-3-hexen-1-ol, used as starting product in the process described above, can be prepared from 2-methyl-4-(2,5,6,6-tetramethyl-2-cyclohexen-1-yl)-2-buten-1-al following the method described in the preceding examples. The cited aldehyde was prepared from cis- and trans-irone, according to the following procedure.

5 g of trans-irone, 4 g of ethyl chloroacetate and 20 ml of absolute ether were treated under argon with potassium tert-butylate, prepared from 50 ml of tert-butanol and 4.3 g of potassium. The reaction was done at room temperature. After leaving to react at this temperature for one night, the reaction mixture was concentrated under vacuum and then extracted with ether. The residue obtained was mixed with 10 ml of 10% soda and 30 ml of ethanol, and then maintained at reflux for 1 h. After acidification and extraction with ether, the organic extracts were combined and, after the usual treatments, yielded, at b.p. 150°/10 Pa, 2.7 g of the desired trans-aldehyde.

The cis-isomer of this same aldehyde was obtained following the same method as indicated above but starting from the irone of cis-configuration. The various isomers of methyl-AMBROX, obtained as indicated above, are novel chemical entities possessing interesting organoleptic properties, with an amber or woody-amber character, and can therefore be used in perfumery.

EXAMPLE 4

Acid cyclization of (E)- and (Z)-1,4-dimethyl-6-(2,6,6-trimethyl-1-cyclohexen-1-yl)-3-hexen-1-ol The reaction was carried out according to the process described in Example 1, by means of 95% sulphuric acid and at −20°. To this end, a solution of the above-mentioned alcohol (isomeric mixture E/Z 1.5:1, 4.2 g, 0.017 mol) in CH$_2$Cl$_2$ (10 ml) was treated with 4.3 g of $H_2SO_4$ (0.042 mol) in 40 ml of $CH_2Cl_2$. After 3 h at −20°, the mixture was poured into cold saturated aqueous $NaHCO_3$ solution (100 ml). The phases were separated and the aqueous phase was extracted with $Et_2O$ (3×20 ml). The combined organic phase was dried ($Na_2SO_4$), concentrated and the residual oil distilled i.v. to afford a colorless oil (4.07 g) which was purified by column chromatography [silica gel (350 g, toluene-/ethyl acetate 19:1, then ethyl acetate] to give a mixture of 12-methyl-AMBROX and 12-methyl-epi-AMBROX (2.92 g, yield 77%). The following table summarizes the results obtained in this experiment as well as those obtained in the similar cyclization of starting alcohols of (E)- or (Z)-configuration.

TABLE

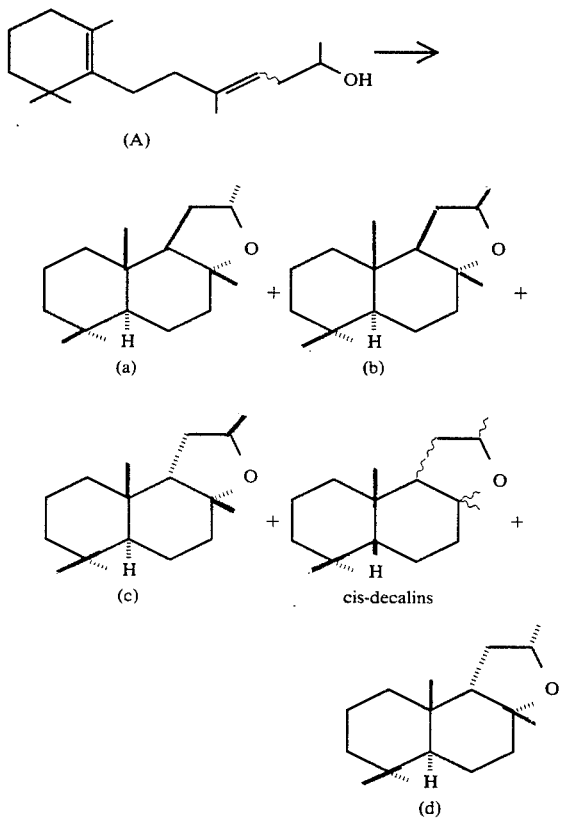

| Starting alcohol | Products/Yields (%) | | | | |
|---|---|---|---|---|---|
| | a | b | c | d | cis-decalins |
| (E)-A | 25 | 20 | 8 | 4 | 11 |
| (Z)-A | 2 | 2 | 26 | 23 | 12 |
| (E/Z 1.5:1)-A | 17 | 15 | 19 | 12 | 12 |

Analytical data a  2β,3aα,5aβ,9aα,9bβ-dodecahydro-2,3a,6,6,9a-pentamethyl-naphtho[2,1-b]furan
  $^1$H-NMR(360MHz): 0.83(6H, 2s); 0.88(3H, s); 1.11(3H, s); 1.19(3H, d, J=7Hz); 4.21(1H, m)δppm
  MS: 250(0.5, M+), 235(100), 217(8), 151(10), 137(36), 111(52), 95(34), 81(41)

b  2α,3aα,5aβ,9aα,9bβ-dodecahydro-2,3a,6,6,9a-pentamethyl-naphtho[2,1-b]furan
  $^1$H-NMR(360MHz): 0.83(3H, s); 0.85(3H, s); 0.87(3H, s); 1.14(3H, s); 1.29(3H, d, J=7Hz); 4.07(1H, m)δppm
  MS: 250(3, M+), 235(100), 217(8), 151(8), 137(37), 111(56), 95(36)

c  2α,3aα,5aβ,9aα,9bα-dodecahydro-2,3a,6,6,9a-pentamethyl-naphtho[2,1-b]furan
  $^1$H-NMR(360MHz): 0.81(3H, s); 0.89(3H, s); 1.09(3H, s); 1.16(3H, d, J=7Hz); 1.37(3H, s); 4.11(1H, m)δppm
  MS: 250(6, M+), 235(85), 151(30), 137(100), 111(57), 95(58), 81(60), 43(98)

d  2β,3aα,5aβ,9aα,9bα-dodecahydro-2,3a,6,6,9a-pentamethyl-naphtho[2,1-b]furan
  $^1$H-NMR(360MHz): 0.81(3H, s); 0.89(3H, s); 1.09(3H, s); 1.26(3H, d, J=7Hz); 1.37(3H, s);4.04(1H, m)δppm
  MS: 250(8, M+)235(46), 151(46), 137(95), 109(52), 95(48), 81(58), 43(100)

The alcohols used as starting materials in the process described above were prepared from 4-methyl-6-(2,6,6-trimethyl-1-cyclohexen-1-yl)-3-hexen-1-ol (see Example 1) following the method described [see Swern, J. Org. Chem. 43, 2480 (1978)].

A solution of DMSO (2.2 g) in $CH_2Cl_2$ (7 ml) was added within 5 min to a stirred solution of oxalyl chloride (1.8 g, 14.2 mmol) in $CH_2Cl_2$ (30 ml) at −50°. After 3 min, a solution of 4-methyl-6-(2,6,6-trimethyl-1-cyclohexen-1-yl)-3-hexen-1-ol (E/Z 1.5:1; 3 g, 12.7 mmol) in $CH_2Cl_2$ (13 ml) was added within 5 min and the mixture was allowed to stir at −50°→−30° during 2 h. Work-up was effected by addition of $(C_2H_5)_3N$ (6.5 g, 64.3 mmol) followed by an aqueous extraction with $CH_2Cl_2$. The crude product, consisting of a 1.5:1 E/Z mixture of corresponding aldehyde having the following analytical data, was used without purification in the next reaction step.

isomer (E):
$^1$H-NMR(360 MHz): 3.14(2H,d,J=7 Hz); 9.66(1H,m) δ ppm.
MS: 234(6,M+), 201(7), 178(9), 160(11), 145(18), 137(27), 123(77), 110(67), 95(99), 81(100).

isomer (Z):
$^1$H-NMR(360 MHz): 3.16(2H,d,J=7 Hz); 9.66(1H,m) δ ppm.
MS: 234(2,M+), 201(2), 160(2), 145(5), 137(81), 121(16), 109(11), 95(100), 81(75).

The above-mentioned crude product was then dissolved in $(C_2H_5)_2O$ (10 ml) and the solution was added dropwise within 5 min to a freshly prepared solution of $CH_3MgI$ (15 mmol) in $(C_2H_5)_2O$ (30 ml) at 0°-10°. After 1 h at r.t., the mixture was poured onto cold 10% aqueous $NH_4Cl$ solution and extracted with ether. Work-up afforded the desired alcohols (E/Z 1.5:1) (2.2 g), readily separated by chromatography (silica gel).

(Z)-1,4-dimethyl-6-(2,6,6-trimethyl-1-cyclohexen-1-yl)-3-hexen-1-ol $R_f$ 0.25 (toluene/ethyl acetate 9:1).
IR: 3530, 3390 (broad), 1434, 1360, 1340, 1240, 1100, 1050, 1030, 920 cm$^{-1}$.
$^1$H-NMR(360 MHz,$D_2O$): 1.02(6H,s); 1.20(3H,d,J=7 Hz); 1.42(2H,m); 1.57(2H,m); 1.65(3H,s); 1.79(3H,s); 1.92(2H,t,J=7 Hz); 1.96-2.12(4H); 2.18(2H,m); 3.79(1H,m); 5.14(1H,t,J=7 Hz) δ ppm.
$^{13}$C-NMR: 139.6(s); 137.1(s); 127.3(s); 120.3(d); 68.0(d); 39.9(t); 38.0(t); 35.0(s); 32.9(t); 32.8(t); 28.7(2q); 27.3(t); 23.5(q); 22.9(q); 19.9(d); 19.6(t) δ ppm.
MS: 250(0,M+), 137(95), 121(17), 107(18), 95(100), 81(74), 69(28).

(E)-1,4-dimethyl-6-(2,6,6-trimethyl-1-cyclohexen-1-yl)-3-hexen-1-ol $R_f$ 0.21 (toluene/ethyl acetate 9:1).
IR: 3540, 3390 (broad), 1440, 1370, 1350, 1250, 1110, 1036, 922 cm$^{-1}$.

¹H-NMR(360 MHz,D₂O): 1.00(6H,s); 1.20(3H,d,J=7 Hz); 1.42(2H,m); 1.57(2H,m); 1,61(3H,s); 1.69(3H,s); 1.91(2H,t,J=7 Hz); 2.07(4H,s); 2.18(2H,m); 3.81(1H,m); 5.20(1H,t,J=7 Hz) δ ppm.

¹³C-NMR: 139.8(s); 137.1(s); 127.1(s); 119.4(d); 68.0(d); 40.5(t); 39.9(t); 38.0(t); 35.0(s); 32.8(t); 28.7(2q); 28.0(t); 22.8(q); 19.8(q); 19.6(t); 16.4(q) δ ppm.

MS: 250(1,M⁺), 137(97), 121(19), 107(15), 95(100), 81(81), 69(25).

EXAMPLE 5

Acid cyclization of (E)- and (Z)-5methyl-7-(2,6,6-trimethyl-1-cyclohexen-1-yl)-4-hepten-1-ol The reaction was carried out according to the process described in Example 1, using 95% sulphuric acid, at −20° under nitrogen. To this end, a solution of (E)- or (Z)-5-methyl-7-(2,6,6-trimethyl-1-cyclohexen-1-yl)-4-hepten-1-ol (2.1 g, 8.1 mol) in CH₂Cl₂ (5 ml) was treated with 2.1 g of H₂SO₄ (0.02 mol) in 21 ml of CH₂Cl₂. After 3 h stirring the mixture was poured into 10% aqueous NaHCO₃ solution (50 ml). Extraction (Et₂O), work-up and bulb-to-bulb distillation i.v. afforded a pale yellow oil which was purified by column chromatography [silica gel (370 g), cyclohexane/ethyl acetate 7:3].

The product thus obtained contained several isomers of ambra oxide, or dodecahydro-4a,7,7,10a-tetramethyl-1H-naphtho[2,1-b]pyran, as well as uninteresting side products.

Amongst said isomers, the following structures were identified:

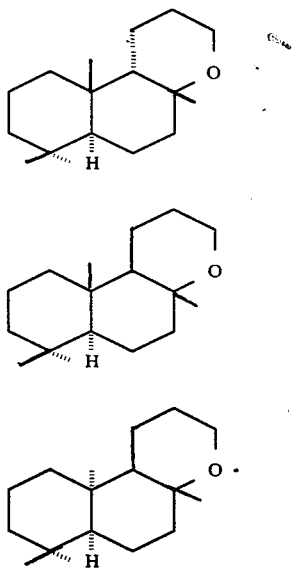

(a)

(b)

(c)

Two other compounds, (a) and (c) diastereoisomers, were detected in weak amounts and their structure was not identified. The following table summarizes the results obtained.

TABLE

| Starting alcohol | Products/Yields (%) | | | |
|---|---|---|---|---|
| | a | b | c | other isomers |
| (E) | 3 | 16 | 2 | 3 |
| (Z) | 6 | 25 | 2 | — |

TABLE-continued

Analytical data a 4aα,6aβ,10aα,10bα-dodecahydro-4a,7,7,10a-tetramethyl-1H-naphtho[2,1-b] pyran
R_f(cyclohexane/ethyl acetate 7:3): 0.60
¹H-NMR(360 MHz): 0.80(3H, s); 0.87(3H, s); 1.12(3H, s); 1.39(3H, s) δ ppm
MS: 250(15, M⁺), 235(55), 137(100), 111(92), 95(77), 81(76)

b 4aα,6aβ,10aα,10bβ-dodecahydro-4a,7,7,10a-tetramethyl-1H-naphtho[2,1-b] pyran
M.p. 81-83°
R_f(cyclohexane/ethyl acetate 19:1): 0.32
IR: 2920, 2850, 1446, 1380, 1364, 1120, 1078, 980 cm⁻¹
¹H-NMR(360 MHz): 0.75(3H, s); 0.80(3H, s); 0.87(3H, s); 0.90–1.80 (16H); 1.25(3H, s); 3.65(2H) δ ppm
¹³C-NMR: 74.6(s); 60.8(t); 57.8(d); 56.4(d); 42.1(t); 42.0(t); 39.0(t); 36.9(s); 33.3(q); 33.3(s); 27.7(t); 21.3(q); 19.9(q); 19.9(t); 18.6(t); 18.1(t); 15.5(q) δ ppm
MS: 250(0.5, M⁺), 235(100), 137(32), 111(75), 95(43), 81(48), 69(40), 55(46), 43(55)

c 4aα,6aβ,10aβ,10bβ-dodecahydro-4a,7,7,10a-tetramethyl-1H-naphtho[2,1-b] pyran
R_f(cyclohexane/ethyl acetate 19:1): 0.32
MS: 250(1, M⁺), 235(100), 137(26), 121(27), 111(82), 95(42), 81(49)

The alcohols used as starting materials in the process described above were prepared by an alternative method to that represented in Scheme I, using conventional reactions. They were prepared from dihydro-β-ionone, as follows.

A solution of 4-(2,6,6-trimethyl-1-cyclohex-1-yl)-2-butanone (150 g, 0.77 mol) in THF (500 ml) was added dropwise within 40 min to a stirred solution of vinylmagnesium bromide [0.93 mol: freshly prepared from Mg (22,3 g, 0.93 mol) and vinyl bromide (100 g, 0.93 mol)] in THF (1 l) at reflux under N₂. After the addition the mixture was heated at reflux during 1 h, cooled and then saturated aqueous NH₄Cl solution (250 ml) and H₂O (300 ml) were cautiously added dropwise. The phases were separated and the aqueous phase was extracted with Et₂O. The combined organic phase was washed with H₂O and saturated aqueous NaCl solution, dried (Na₂SO₄), concentrated and fractionally distilled i.v. to afford 3-methyl-5-(2,6,6-trimethyl-1-cyclohexyl)-1-penten-3-ol as a colorless oil (151 g, 88%).

B.p. 85°-88°/20 Pa.
R_f(toluene/ethyl acetate 19:1): 0.26.
IR: 3410 (broad), 1475, 1456, 1410, 1360, 1104, 998, 910 cm⁻¹.
¹H-NMR(360 MHz,D₂O):; 0.98(6H,s); 1.31(3H,s); 1.41(2H,m); 1.58(3H,s); 1.50–1.65(4H); 1.89(2H,t,J=6.5 Hz); 2.01(2H,m); 5.08(1H,d,J=11 Hz); 5.23(1H,d, J=18 Hz); 5.95(1H,dd,J=18,11 Hz) δ ppm.
MS: 222(3,M⁺), 204(10), 189(31), 133(28), 121(54), 107(31), 95(100), 81(56), 71(33), 55(39), 41(48).

The mixture of the alcohol prepared above (25 g, 0.104 mol), trimethyl orthoacetate (72 g, 0.6 mol) and propionic acid (0.4 g, 5.4 mmol) was heated at reflux during 4 h whilst gradually increasing the external oil-bath temperature (135°→150°) and continually distilling of (50 cm Vigreux column) the volatile reaction components [MeOH+MeC(OMe)₃]. After 4 h, the internal temperature was 116°-117° and the mixture was cooled to r.t. prior to the addition of a second portion of propionic acid (0.4 g). The mixture was now re-heated at reflux during 20 h (oil-bath temperature: 140°; internal temperature: 117°-119°) whilst again continually removing the volatile components. The residual oil was distilled first at atmospheric pressure to remove excess MeC(OMe)₃ (impure: 46 g, b.p. 108°-110°/9.8×10⁴ Pa) and then at 6.7 Pa to afford unreacted starting alcohol (4 g, i.e. 83% conversion) (B.p. 73°/6.7 Pa) and crude methyl 5-methyl-7-(2,6,6-trimethyl-1-cyclohexen-1-yl)-4-heptenoate (E/Z 1.3:1) as a colorless oil (23.5 g).

B.p. 110°-118°/6.7 Pa.

IR: 2910, 1438, 1360, 1250, 1200, 1160, 986, 890 cm$^{-1}$.

isomer (E):

$R_f$(toluene): 0.31.

$^1$H-NMR(360 MHz): 0.99(6H,s); 1.42(2H,m); 1.55-1.65(2H); 1.60(3H,s); 1.66(3H,s); 1.90(2H,t,J=7 Hz); 1.95-2.12(4H); 2.34(4H); 3.67(3H,s); 5.12(1H,broad t,J=7 Hz) δ ppm.

MS: 278(0.5,M+), 137(99), 121(13), 109(15), 95(100), 81(87), 67(26), 55(21).

isomer (Z):

$R_f$(toluene): 0.35.

$^1$H-NMR(360 MHz): 1.02(6H,s); 1.42(2H,m); 1.55-1.65(2H); 1.65(3H,s); 1.74(3H,s); 1.92(2H,t,J=7 Hz); 1.95-2.12(4H); 2.34(4H); 3.67(3H,s); 5.07(1H,broad t,J=7 Hz) δ ppm.

MS: 278(1,M+), 137(96), 121(13), 109(12), 95(100), 81(87), 67(28), 55(23).

A solution of the ester isomeric mixture obtained above (E/Z 1.3:1, 18 g, 0.063 mol) in Et$_2$O (100 ml) was added dropwise within 15 min to a slurry of LiAlH$_4$ (3.2 g, 0.084 mol) in Et$_2$O (100 ml) at reflux under N$_2$. To the cooled mixture was then successively added H$_2$O (3.2 ml), 20% aqueous NaOH solution (3.2 ml) and H$_2$O (10 ml). Filtration (Hyflo), concentration of the filtrate and distillation i.v. afforded 5-methyl-7-(2,6,6-trimethyl-1-cyclohexen-1-yl)-4-hepten-1-ol (E/Z 1.3:1) as a viscous colorless oil (15.5 g, yield 98%). B.p. 113°-123°/6.7 Pa. Column chromatography [silica gel (2×800 g), toluene-/ethyl acetate 9:1] of 12 g afforded pure samples of (E)- and (Z)-heptenol.

(E)-5-methyl-7-(2,6,6-trimethyl-1-cyclohexen-1-yl)-4-hepten-1-ol

IR: 3320(broad), 1440, 1380, 1360, 1200, 1060, 878 cm$^{-1}$.

$^1$H-NMR(360 MHz,D$_2$O): 1.00(6H,s); 1.41(2H,m); 1.57(2H,m); 1.60(3H,s); 1.63(2H,m); 1.66(3H,s); 1.91(2H,t,J=6 Hz); 1.97-2.13(6H); 3.65(2H,t, J=7 Hz); 5.17(1H,t,J=7 Hz) δ ppm.

$^{13}$C-NMR: 137.2(s); 136.9(s); 127.0(s); 123.2(d); 62.7(t); 40.3(t); 39.9(t); 35.0(s); 32.8(t); 28.7(2q); 28.0(t); 24.3(t); 19.8(q); 19.6(t); 16.0(q) δ ppm.

MS: 250(2,M+),137(76), 121(25), 95(100), 81(74),67(31), 55(30).

(Z)-5-methyl-7-(2,6,6-trimethyl-1-cyclohexen-1-yl)-4-hepten-1-ol

IR: 3320(broad), 1448, 1380, 1360, 1200, 1060 cm$^{-1}$.

$^1$H-NMR(360 MHz,D$_2$O): 1.02(6H,s); 1.42(2H,m); 1.57(2H,m); 1.62(2H,m); 1.64(3H,s); 1.74(3H,d,J=1.5 Hz); 1.92(2H,broad t,J=6 Hz); 1.97-2.14(6H); 3.64(2H,t,J=7 Hz); 5.12(1H,t,J=7 Hz) δ ppm.

$^{13}$C-NMR: 137.2(s); 136.6(s); 127.1(s); 124.2(d); 62.6(t); 40.0(t); 35.0(s); 33.2(t); 32.9(t); 32.7(2t); 28.7(2q); 27.4(t); 24.4(t); 23.3(q); 19.9(q); 19,6(t) δ ppm.

MS: 250(2,M+), 137(78), 121(23), 95(100), 81(81), 67(29), 55(30).

What we claim is:

1. A process for the preparation of polycyclic ethers of formula

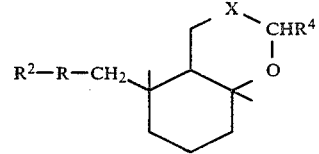

wherein x represents —(CH$_2$)$_n$—, index n stands for integer 0 or 1, symbol R$^4$ designates a hydrogen atom or a methyl radical, symbol R$^2$ represents a hydrogen atom or a lower alkyl radical from C$_1$ to C$_3$ and R designates a C$_1$ to C$_6$ linear or branched alkyl radical, which process comprises the cyclization by means of an acidic agent, in an inert organic solvent at a temperature of between −60° and +30° C., of an unsaturated compound of formula

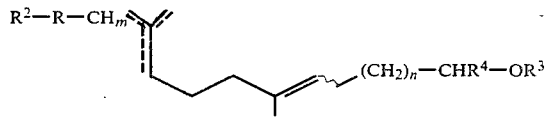

having a double bond in one of the positions indicated by the dotted lines, and wherein index m defines an integer number equal to 1 or 2, symbol R$^3$ stands for a hydrogen atom or a protecting group of the hydroxyl function bound to the oxygen atom and able to disassociate itself from the latter under the reaction conditions, the wavy line represents a C—C bond of cis or trans configuration and index n and symbols R, R$^2$ and R$^4$ are defined as above.

* * * * *